(12) United States Patent
    Viebach

(10) Patent No.: US 7,823,457 B2
(45) Date of Patent: Nov. 2, 2010

(54) PRESSURE GAUGE

(75) Inventor: Thomas Viebach, Pischershofen (DE)

(73) Assignee: Invendo Medical GmbH, Weinheim (DE)

(*) Notice: Subject to any disclaimer, the term of this patent is extended or adjusted under 35 U.S.C. 154(b) by 381 days.

(21) Appl. No.: 12/060,967

(22) Filed: Apr. 2, 2008

(65) Prior Publication Data
    US 2008/0245153 A1   Oct. 9, 2008

(30) Foreign Application Priority Data
    Apr. 3, 2007   (DE) .................. 10 2007 000 200

(51) Int. Cl.
    *G01L 9/12* (2006.01)
(52) U.S. Cl. .......................... 73/718; 73/756
(58) Field of Classification Search .............. None
    See application file for complete search history.

(56) References Cited

U.S. PATENT DOCUMENTS

| 3,418,853 | A |   | 12/1968 | Curtis |
| 3,795,140 | A |   | 3/1974 | Nishihara |
| 4,167,122 | A | * | 9/1979 | Siegel ..................... 73/706 |
| 4,993,266 | A | * | 2/1991 | Omura et al. ............... 73/720 |
| 5,000,049 | A |   | 3/1991 | Cooper et al. |
| 5,259,364 | A |   | 11/1993 | Bob et al. |
| 5,317,917 | A | * | 6/1994 | Dufour .................... 73/702 |
| 5,499,535 | A | * | 3/1996 | Amano et al. .............. 73/717 |
| 5,756,900 | A |   | 5/1998 | Arie et al. |
| 6,077,219 | A |   | 6/2000 | Viebach et al. |
| 6,575,040 | B2 |   | 6/2003 | Dietrich |
| 6,649,046 | B2 |   | 11/2003 | Chevallet |
| 6,684,710 | B2 |   | 2/2004 | Chevallet et al. |
| 6,889,556 | B2 |   | 5/2005 | Steger |
| 7,181,974 | B2 | * | 2/2007 | Hegner et al. .............. 73/724 |
| 7,258,014 | B2 | * | 8/2007 | Rudkin .................... 73/702 |
| 7,418,871 | B2 | * | 9/2008 | Moelkner et al. ........... 73/754 |
| 7,421,903 | B2 | * | 9/2008 | Brosh ..................... 73/722 |

FOREIGN PATENT DOCUMENTS

| DE | 2823670 A1 | 12/1979 |
| DE | 4219888 C2 | 1/2003 |
| DE | 10329159 A1 | 1/2005 |
| WO | 98/47424 A1 | 10/1998 |

* cited by examiner

*Primary Examiner*—Lisa M Caputo
*Assistant Examiner*—Jermaine Jenkins
(74) *Attorney, Agent, or Firm*—Standley Law Group LLP

(57) ABSTRACT

A pressure gauge is composed of two separate components adapted to be assembled and disassembled by hand. The one component is a pressure-motion conversion element (3, 6) for receiving a pressure and effecting a movement of a movable portion (3c, 6c) thereof in response thereto, and the other component is a force measuring element (5) for measuring a force caused due to the movement of the movable portion (3c, 6c). The pressure-motion conversion element (3, 69) is constructed as a disposable component, whereas the force measuring element (5) is intended for re-use.

7 Claims, 5 Drawing Sheets

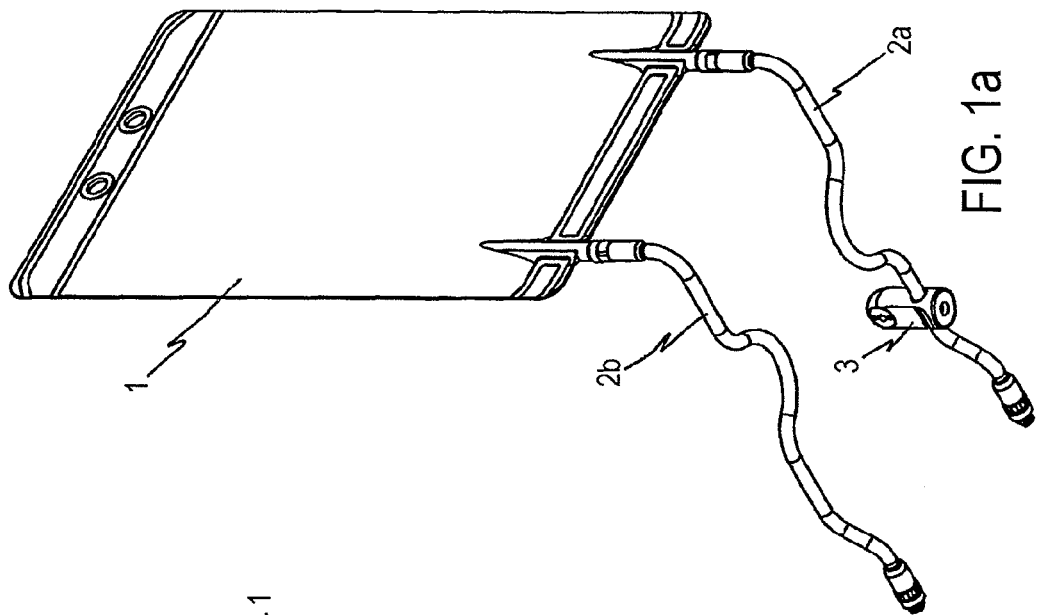
FIG. 1a
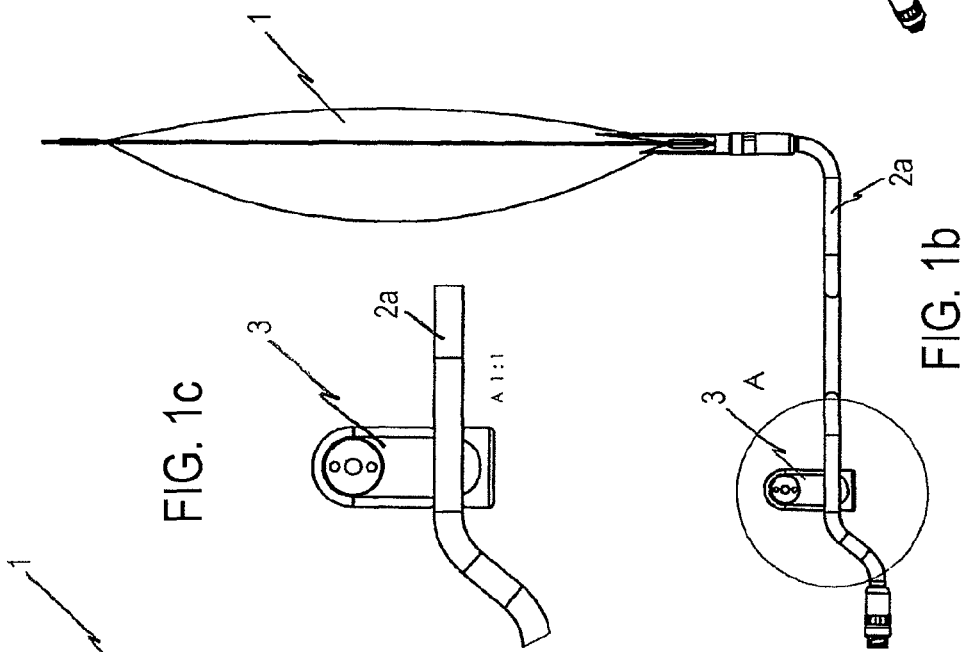
FIG. 1b
FIG. 1c
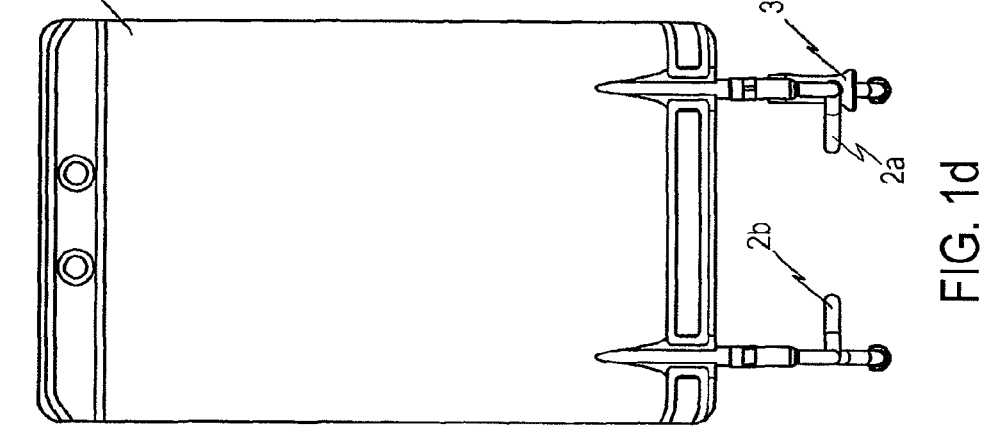
FIG. 1d

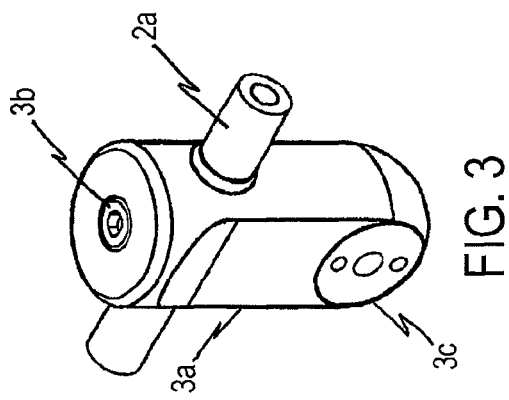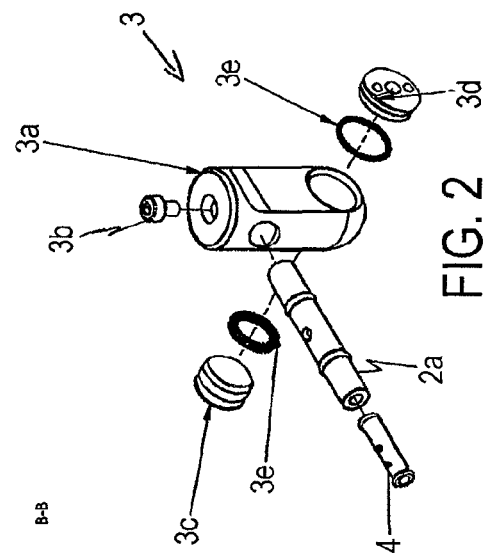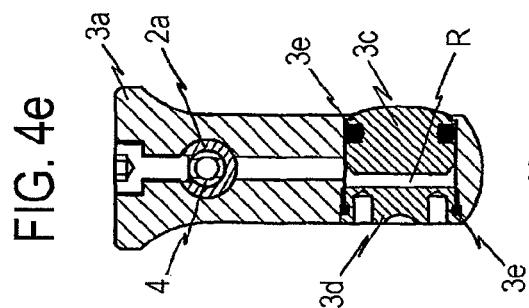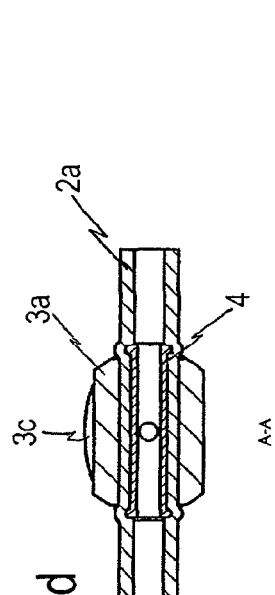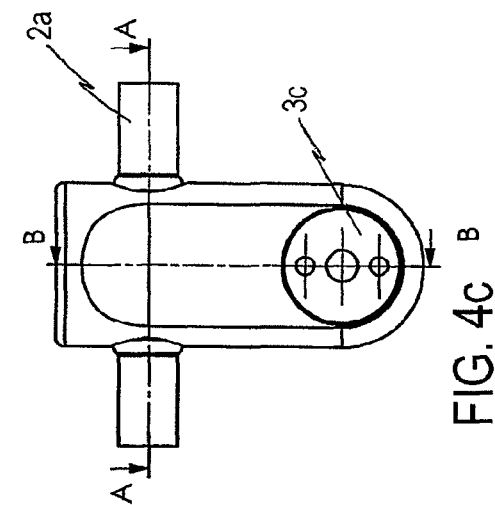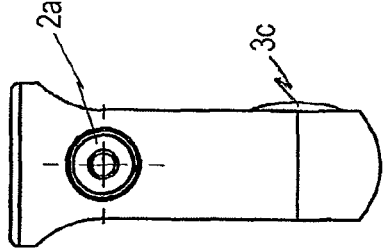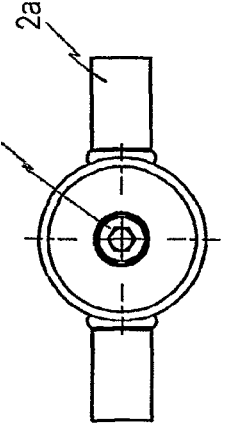

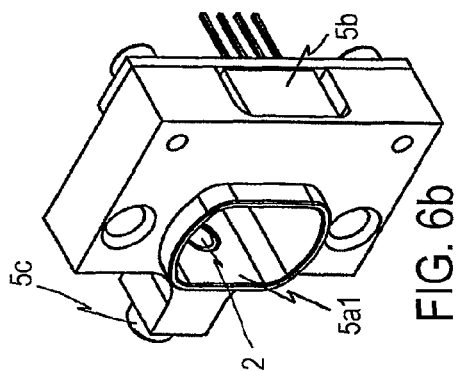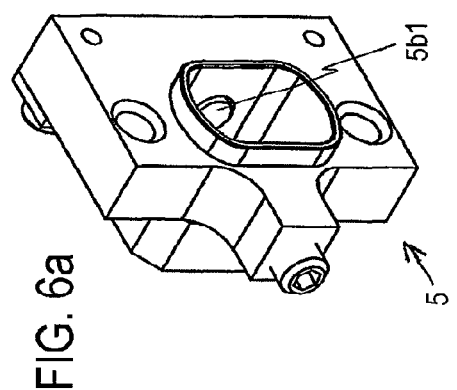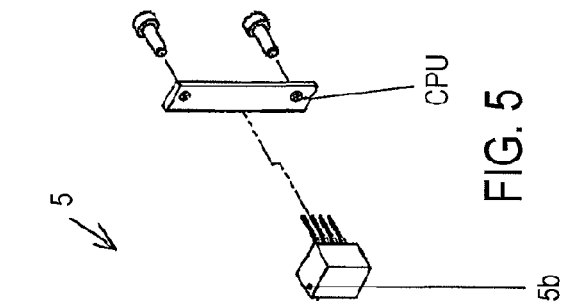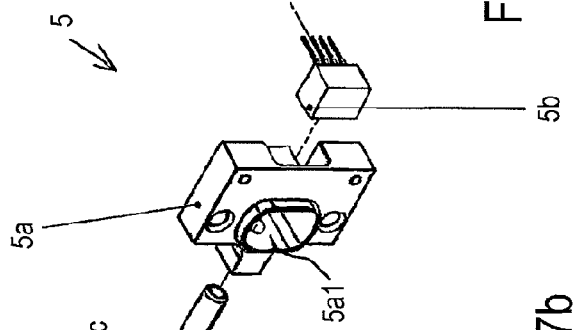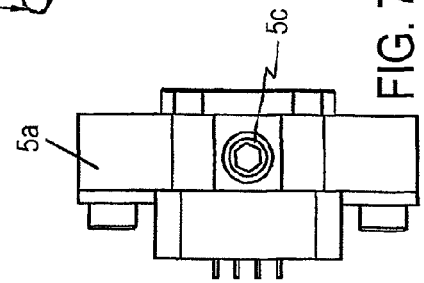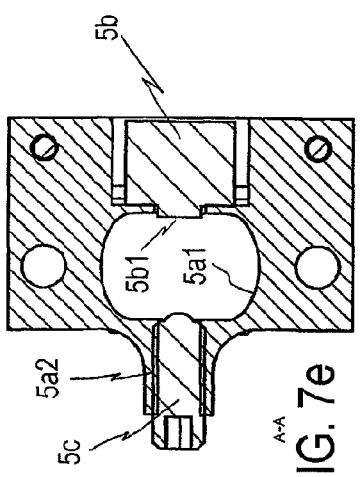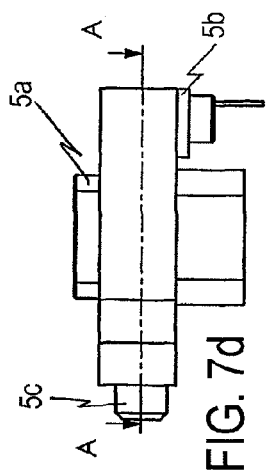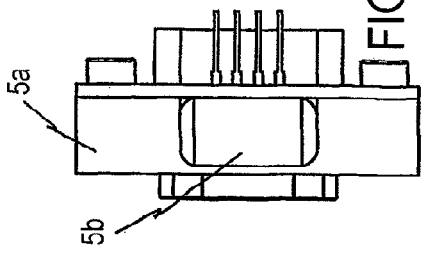

B 2:1

PRESSURE GAUGE

CROSS-REFERENCE TO RELATED APPLICATIONS

This application claims benefit of priority under 35 USC 119(a) to German application 10 2007 000200.0, filed on 3 Apr. 2007, which is incorporated by reference as if fully recited herein.

TECHNICAL FIELD

The present invention relates to a pressure gauge and, in particular, to a pressure gauge for measuring a fluid pressure.

BACKGROUND OF THE ART

Endoscopic devices and devices for introducing a medical endoscope into a body canal are described, for instance, in U.S. Pat. No. 5,259,364. The devices described in this document permit that an endoscope is no longer pushed into the body to be examined, but moves into the body all by itself. For this purpose, the endoscope is equipped with an inherent drive which allows easier and quicker insertion.

As such an inherent drive, also a so-called everting tube can be used, for instance, with the endoscope shaft being inserted therein. Upon propulsion of the endoscope, different relative motions occur. On the one hand, a relative motion occurs between the endoscope shaft and the everting tube, which are in sliding contact with each other. On the other hand, there is also a relative motion between an inside portion and an outside portion of the unwinding everting tube.

To reduce the respectively occurring sliding friction as well as a static friction between respective elements, the use of a lubricant supplied from the outside has e.g. been suggested, for instance in the U.S. Pat. No. 6,077,219. In both cases, a lubricant adapted to be stored in a fluid bag is supplied between the endoscope shaft and the everting tube, on the one hand, as well as between the two everting tube portions that come to be disposed one above the other, on the other hand. For a check of the pressure of the lubricant supplied to the point of lubrication between the endoscope shaft and the everting tube, the pressure has to be detected by a pressure gauge arranged between the hydraulic fluid bag and the point of lubrication between the endoscope shaft and the everting tube.

If the endoscopic device is formed as a disposable device, use thereof is followed by disposal of all elements of the endoscopic device that might have come into contact with the body fluid of the patient examined, such as the endoscope shaft including everting tube, the fluid bag, and the pressure gauge.

SUMMARY OF THE INVENTION

Technical Problem

It is therefore the object of the invention to provide a simple pressure gauge at a reasonable price, which takes account of a disposable construction of e.g. an endoscopic device.

Technical Solution

The object of the invention is achieved by a pressure gauge comprising the features according to claim 1.

Advantageous further developments of the invention are subject of the dependent claims.

Accordingly, the gist of the invention consists in that the pressure gauge is composed of two separate components adapted to be joined together and to be released in a nondestructive manner. The one component is a pressure-motion conversion element preferably manufacturable at low cost, having a movable portion for receiving a pressure and moving in response thereto, and the other component is a force measuring element for measuring a force exerted by the motion of the movable portion onto the force measuring element. The components are constructed such that, in the functional coupling thereof, only the pressure-motion conversion element with the pressure medium remains isolated. Therefore, the pressure-motion conversion element manufacturable at low cost can be thrown away after a once-only use, whereas the force measuring element, which is more expensive as a rule, can be re-used. Due to this constructional and elementary division of the pressure gauge into a cheap disposable component and a reusable component, it is not required for oneway solutions to throw the entire pressure gauge away, or to demount and clean it, which takes up a great deal of time, but only the component manufacturable at low cost can be thrown away while the other component can be reused.

If the pressure gauge according to the present invention is applied to a disposable endoscopic device, in which the endoscope shaft, the everting tube as well as a fluid bag/container which is fluid-connected to the endoscope by tubes and which stores a lubricant for lubrication between the endoscope shaft and the everting tube as well as inside the everting tube can be thrown away after a one-time use, the pressure-motion conversion element, which is constructed as a disposable, can be separated from the force measuring element and can be thrown away after use. The force measuring element, on the other hand, can be reused. In this way, a favorably priced disposable endoscopic device can be realized.

Preferably, the pressure-motion conversion element is formed as a gas or fluid tight unit in order to prevent a discharge of gas or fluid into the environment, as it is particularly required in endoscopic applications.

The pressure-motion conversion element preferably has a receiving portion for receiving a portion of a container or tube in order to detect the pressure of a fluid or gas flowing inside the container or tube.

In an advantageous embodiment of the invention, the receiving portion receives a tube portion of a tube, which is connected to a disposable fluid bag for storing a fluid. Preferably, the tube portion itself is used for forming a fluid-tight connection between itself and the receiving portion.

Preferably, the movable portion of the pressure-motion conversion element is a piston or a membrane. It may, however, be any other element moving upon change of a pressure acting thereon, such as a lever supported by a hinge, etc. The movement of the movable portion is not restricted to a translatory motion, but can be any movement whatsoever, e.g. translation, rotation, or a combination of translation and rotation.

Preferably, the force measuring element is a force measuring sensor converting the measured force into electrical signals, such as a piezo-element. The force measuring element may, however, work according to another principle, for instance in a purely mechanical manner, as long as it is ensured that the pressure applied to the pressure-motion conversion element can be inferred from the force measured by the force measuring element.

Advantageously, the force measuring element or the pressure-motion conversion element is provided with a positioning means for positioning the pressure-motion conversion element in its assembled state relative to the force measuring element in a predetermined position.

Moreover, the force measuring element or the pressure-motion conversion element can be advantageously provided with a locking mechanism for fixing the pressure-motion conversion element in its assembled state relative to the force measuring element.

BRIEF DESCRIPTION OF THE DRAWINGS

Hereinafter the invention shall be specified in detail by means of a preferred embodiment with reference to the accompanying drawings, in which identical parts are identified by identical reference numbers and wherein:

FIG. 1a is a perspective view of a fluid bag having connecting tubes one of which is provided with a pressure-motion conversion element;

FIG. 1b is a side view of the FIG. 1a fluid bag;

FIG. 1c is an enlarged representation of detail A from FIG. 1b;

FIG. 1d is a rear view of the FIG. 1a fluid bag;

FIG. 2 is an exploded view of a first embodiment of a pressure-motion conversion element;

FIG. 3 is an assembled perspective view of the FIG. 2 pressure-motion conversion element;

FIG. 4a is a top view of the FIG. 3 pressure-motion conversion element;

FIG. 4b is a side view of the FIG. 3 pressure-motion conversion element;

FIG. 4c is a front view of the FIG. 3 pressure-motion conversion element;

FIG. 4d is a sectional view of the FIG. 3 pressure-motion conversion element, taken along line A-A of FIG. 4c;

FIG. 4e is a sectional view of the FIG. 3 pressure-motion conversion element, taken along line B-B in FIG. 4c;

FIG. 5 is an exploded view of an embodiment of a force measuring element;

FIGS. 6a and 6b are perspective views of the FIG. 5 force measuring element;

FIG. 7a is a top view of the FIG. 5 force measuring element;

FIGS. 7b and 7c are side views of the FIG. 5 force measuring element;

FIG. 7d is a top view of the FIG. 5 force measuring element;

FIG. 7e is a side view of the FIG. 5 force measuring element, taken along line A-A of FIG. 7d;

FIG. 11e is a sectional view of the FIG. 10 pressure-motion conversion element, taken along line A-A of FIG. 11a.

DETAILED DESCRIPTION OF THE PREFERRED EMBODIMENT

Figure 9F:
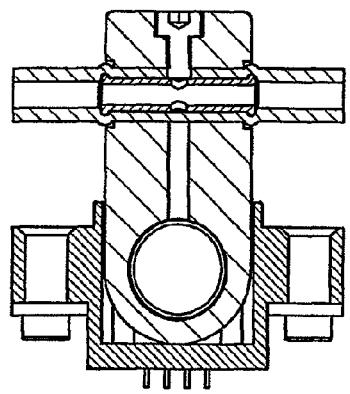
FIG. 9f is an assembled sectional view of the FIG. 8a pressure gauge, taken along line A-A of FIG. 9d.
Figure 8A:
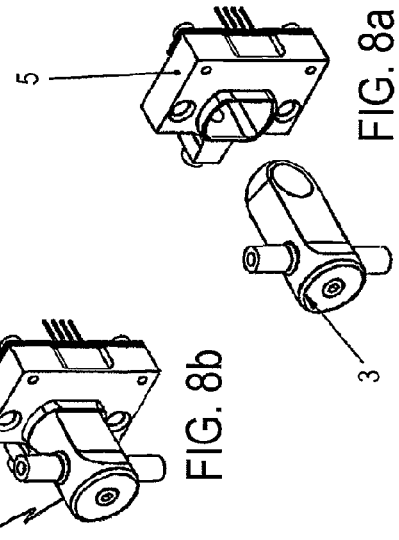
FIGS. 8a and 8b are perspective views of a non-assembled embodiment of the pressure gauge.
Figure 9D:
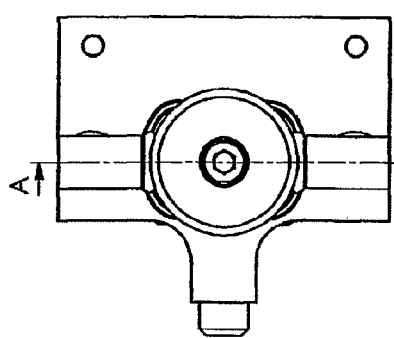
FIG. 9d is an assembled front view of the FIG. 8a pressure gauge.
Figure 8B:
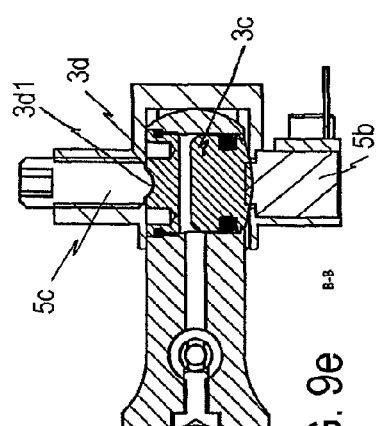
Figure 9C:
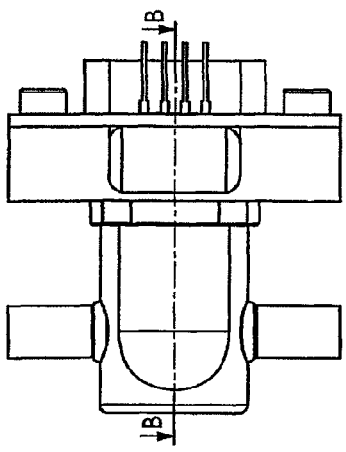
FIG. 9c is an assembled side view of the FIG. 8a pressure gauge.
Figure 9B:
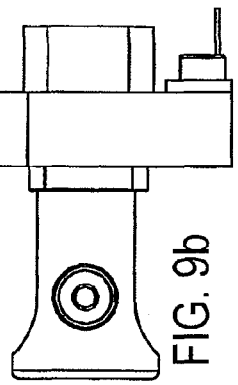
FIG. 9b is an assembled top view of the FIG. 8a pressure gauge.
Figure 9E:
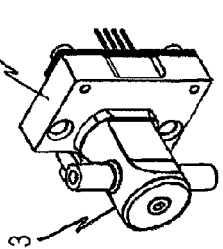
FIG. 9e is an assembled sectional view of the FIG. 8a pressure gauge, taken along line B-B of FIG. 9c.
Figure 9A:
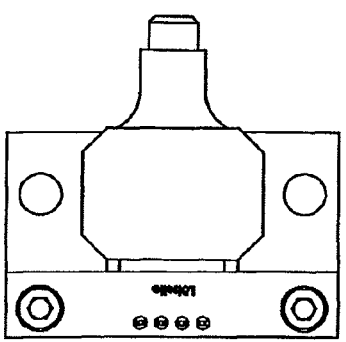
FIG. 9a is an assembled rear view of the FIG. 8a pressure gauge.

FIGS. 1a, 1b, and 1d show a hydraulic fluid bag 1 used for storing lubricants, such as oil, water, an oil-water emulsion, etc. for an endoscopic device. The fluid bag 1 comprises two connecting tubes 2a, 2b, particularly silicone tubes, via which the lubricant (preferably liquid) or fluid is fed to an endoscope. Specifically, the fluid from the fluid bag 1 is conducted to the points of lubrication, for instance by means of a centrifugal pump, into which the connecting tubes 2a, 2b are inserted and which makes fluid in the connecting tubes 2a, 2b move. A lubricant is fed, e.g. via the connecting tube 2b, to a lubricating point between the inner surfaces of an everting tube or into the everting tube of an endoscope, whereas, via the connecting tube 2a, a lubricant is fed to a lubricating point between the endoscope shaft and the outer surfaces of the everting tube abutting on the endoscope shaft.

In order to measure the pressure by which lubricant is fed to the lubricating point through the tube 2a, a pressure-motion conversion element 3 is attached to the tube 2a, and forms a pressure gauge of the invention together with a force measuring element 5 which shall be described below.

A pressure-motion conversion element 3 according to a first embodiment is shown in FIG. 2 in an exploded view and in FIG. 3 in a perspective view. The pressure-motion conversion element 3 according to the first embodiment is essentially composed of an elongated housing 3a having an elongated hole and two cross holes arranged perpendicularly to each other, wherein the cross holes are connected to each other via the elongated hole, a closing member 3b, a piston 3c, a plug 3d as well as two seal rings 3e. The housing 3a, closing member 3b, piston 3c as well as a plug 3d are preferably producible from plastic and by injection molding.

As is shown in FIGS. 2 and 4e, which is a sectional view of the pressure-motion conversion element 3 along line B-B in FIG. 4c, the elongated hole extends from the top surface of the housing through the upper cross hole, and opens into the lower cross hole. The opening formed by the elongated hole in the top surface of the housing is fluid-tightly closed by a closing member 3b, which is formed as a screw in this embodiment.

With respect to FIGS. 3 and 4b, one side of the lower cross hole is closed by the plug 3d which is fitted in or rather screwed into the housing 3a, wherein a seal 3f is provided between the housing 3a and the plug 3d for a fluid-tight sealing. At the other side of the lower cross hole, a movable element 3c is fluid-tightly fitted in. In this way, a pressure chamber R is formed in the lower cross hole between the plug 3d and the movable element 3c, as is shown in FIG. 4e. In this embodiment, the movable element 3c is formed as a piston surrounded by a seal 3f, said piston being arranged in an axially shiftable manner in the lower cross hole. The front end of the piston 3d facing the pressure chamber R is a pressure receiving surface. The front end of the piston 3d, facing away from the pressure chamber R, bulges out of the outer side of the housing.

As is shown in FIGS. 2, 3, 4a-4e, the upper cross hole constitutes a receiving portion of the housing 3a. A portion of the connecting tube 2a is inserted/fitted into the upper cross hole, as is shown in FIGS. 4d and 4e. The connecting tube 2a is fitted into the upper cross hole such that it forms a fluid-tight connection with the housing 3a. In order to reliably maintain this sealing and prevent a partial detachment of the outer surface of the connecting tube from the inner surface of the cross hole, a supporting sleeve 4 is arranged inside the connecting tube 2a, which supports or presses the connecting tube 2a against the inner surface of the upper cross hole. The supporting sleeve 4 is advantageously formed of a flexible plastic in order to apply, in the installation position, a force acting radially outwards to the connecting tube 2a. As is shown in FIG. 4d, the supporting sleeve 4 is advantageously provided at its ends with a projection or is enlarged outwardly, so that the connecting tube is fixed in a predetermined position with respect to the housing 3a. Additionally or alternatively, the connecting tube 2a and the supporting sleeve 4 can also be fixed with respect to the housing 3a by means of the closing member 3b, e.g. by the closing member 3b in its installation position pressing against the outer surface of the connecting tube 2a.

As is shown in FIGS. 4d and 4e, the connecting tube 2a and the supporting sleeve 4 have orifices formed in their radial direction and ending into the elongated housing of the housing 3a. Thus, there is a connection between the inside of the connecting tube 2a and the pressure chamber R via the orifices and the elongated housing.

The above-described connection can be advantageously realized in that, after an insertion of the connecting tube 2a together with the supporting sleeve 4 into the upper cross hole, drilling is effected from the upper side of the housing for simultaneously forming the orifices in the supporting sleeve 4 and in the connecting tube 2a, as well as the elongated housing. In this way, it is ensured that the orifices of the supporting sleeve 4 and of the connecting tube 2a are aligned with the elongated housing for ensuring a reliable connection of the inside of the connecting tube 2a with the pressure chamber R.

The above-described pressure-motion conversion element 3 cooperates with a force measuring element 5 for forming a pressure gauge according to the invention. As is shown in FIG. 5, the force measuring element 5 is essentially composed of a housing 5a, a force measuring sensor 5b, and a positioning means 5c. The housing has an essentially rectangular shape with a projecting portion. As is shown in FIG. 5, the front surface of the housing includes an orifice 5a1 corresponding to the lower area of the pressure-motion conversion element 3. A through hole 5a2 is formed in the side surface of the projecting portion, ending in the orifice 5a1. The positioning means 5c is arranged in the through hole 5a2. In this embodiment, the positioning means 5c is composed of a spring-biased pin pressed by a spring force to a predetermined extent into the inside of the orifice 5a1. Furthermore, in the side of the housing 5a opposite to the projecting portion, a further orifice 5a3 is formed, ending in the orifice 5a1. The force measuring sensor 5b is inserted into the orifice 5a3 such that its force detecting surface 5b1 is disposed inside the orifice 5a1 freely and opposite to the positioning means 5c, as is shown in FIG. 7e. In this embodiment, the force measuring sensor 5b is a sensor converting a force acting on its force detecting surface 5b1 into electrical signals, which can then be evaluated by means of a CPU, as is shown in FIG. 5, or by something similar. Alternatively, however, a mechanical force measuring sensor can be used.

FIGS. 8b, 9a-9f show different views of the pressure gauge of the invention in its assembled state. The cross-sectional view of FIG. 9e reveals that, in the assembled state, the spring-biased pin 5c presses its bulbous end against a recess 3d1 formed in the plug 3d and corresponding to the bulbous form of the pin end in order to press the pressure-motion conversion element 3 in the direction of the force measuring sensor 5b, so that the pressure-motion conversion element 3 is arranged in a predetermined position in the orifice 5a1 of the force measuring element 5. More precisely, the position is such that the bulbous outer surface of the piston abuts on the force detecting surface 5b1 of the force measuring sensor 5b. Preferably, the pressure-motion conversion element 3 is fixed by means of the positioning means 5c such that its housing 3a does not move relatively to the housing 5a of the force measuring element 5 even if the piston moves. Moreover, the spring-biased pin is preferably designed such that it does not raise any problems to manually insert the pressure motion element 3 into the force measuring element 5 and pull it out again.

Additionally or alternatively, either the pressure-motion conversion element 3 or the force measuring element 5 may be provided with a locking mechanism for preventing a separation of the pressure-motion conversion element 3 and the force measuring element 5 in the assembled state. Such a locking mechanism may e.g. be a pin fastened to the force measuring element 5 and adapted to be moved into a locked position, said pin engaging—in the assembled state of the pressure gauge—in a recess formed in the pressure-motion conversion element 3 such that, in the locked position, the pressure-motion conversion element 3 is no longer adapted to be pulled out of the force measuring element 5 by hand.

Hereinafter, the use or operation of the pressure gauge according to the invention shall be described with reference to a disposable endoscopic device.

Before a start of operation of the pressure gauge, the pressure-motion conversion element 3 is connected to the connecting tube 2a of the fluid bag 2 or is pre-mounted to the same, as has been described above with reference to FIGS. 1a-1d, 2, 3, 4a-4e.

The connecting tube 2a is connected to an endoscope in order to deliver lubricant from the fluid bag 2 to the point of lubrication between the endoscope shaft and the outer surface of the everting tube abutting thereon. To this end, the connecting tube is connected to a centrifugal pump or something similar which feeds the fluid in the connecting tube to the point of lubrication at a certain pressure due to external impact on the connecting tube 2a.

In order to measure the pressure of the lubricant supplied, the application of pressure to the fluid in the connecting tube 2a by means of the centrifugal pump is preceded by the pressure-motion conversion element 3 connected to the connecting tube 2a being inserted into the orifice 5a1 of the force measuring element 5 in order to reach the assembled state shown in FIGS. 8b, 9a-9f, in this way and, thus, the operative state of the pressure gauge of the invention. In this state, the bulbous end of the spring-biased pin 5c engages in the recess of the plug 3d1 and presses the pressure-motion conversion element 3 inside the orifice 5a1 in the direction of the force measuring sensor 5b such that the bulbous outer side of the piston 3c abuts on the force receiving surface 5b1 of the force measuring sensor 5b.

The inside of the connecting tube 2a is fluid connected to the pressure chamber R through the orifices in the connecting tube 2a and the supporting sleeve 4, the upper cross hole and the elongated hole. Thus, fluid having the same pressure as fluid in the connecting tube 2a or the fluid container 1 is in the pressure chamber R. Since a pressure application by means of the centrifugal pump has not yet taken place, this state is referred to as "pressure at rest". The fluid at pressure at rest in the pressure chamber R leads to the piston 3c being urged by a certain force in the direction of the force measuring sensor 5b, so that the force measuring sensor 5b registers a force corresponding to the pressure at rest through a surface 5b1 receiving its pressure. The force measuring sensor is now calibrated according to this force, i.e. is adjusted to zero.

Subsequently, pressure is applied to the fluid in the connecting tube by movement of the centrifugal pump. This leads to a pressure change of the fluid in the connecting tube 2a and the pressure chamber R. Due to this pressure change, the force acting on the pressure receiving surface of the piston 3c changes and, in turn, leads to a movement of the piston 3c in the direction of the force measuring sensor 5b. The movement of the piston 3c causes an increase in the force acting on the force detecting surface 5b1 of the force measuring sensor 5b. The force acting on the force measuring sensor 5b is detected and transmitted in the form of electrical signals to an evaluating unit, for instance a CPU. The CPU is adapted to infer from the force measured by the force measuring sensor 5b to a pressure of the fluid in the connecting tube 2a, or rather is adapted to deduce the pressure of the fluid from this force and adjust, in this way, the pressure of the fluid to the desired value by control of the centrifugal pumps on the basis of the detected values.

Upon conclusion of an examination by the endoscopic device, which is a disposable endoscopic device, the pressure-motion conversion element 3 is separated from the force measuring element 5 by being pulled out of the orifice, wherein at least the force measuring element 3, but preferably also the pressure-motion conversion element 3 are not damaged. The pressure-motion conversion element 3 is then adapted to be disposed of together with the endoscope shaft including everting tube, the fluid bag 1 and all connecting lines from the fluid bag to the point of lubrication, which could be contaminated by body fluid of the patient examined, whereas the force measuring element 5, which has not come into contact with the lubricant or body fluid due to the fluid-tight formation of the pressure-motion conversion element 3, is adapted to be re-used.

FIGS. 10, 11a to 11f show a second embodiment of the pressure-motion conversion element according to the invention. The pressure-motion conversion element 6 according to the second embodiment has a similar structure as the pressure-motion conversion element 3 of the first embodiment, and hereinafter only the differences to this first embodiment shall be described.

Figure 11C:
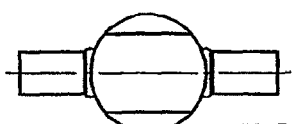
FIG. 11c is a bottom view of the FIG. 10 pressure-motion conversion element.
Figure 11E:
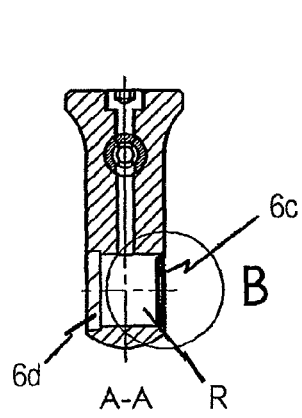
Figure 11A:
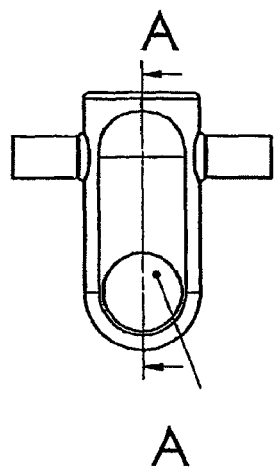
FIG. 11a is a rear view of the FIG. 10 pressure-motion conversion element.
Figure 11D:
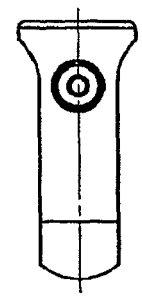
FIG. 11d is a side view of the FIG. 10 pressure-motion conversion element.
Figure 11F:
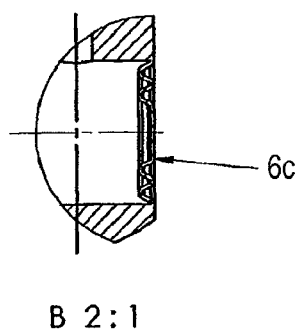
FIG. 11f is an enlarged view of section B in FIG. 11e.
Figure 11B:
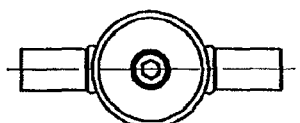
FIG. 11b is a top view of the FIG. 10 pressure-motion conversion element.
Figure 10:
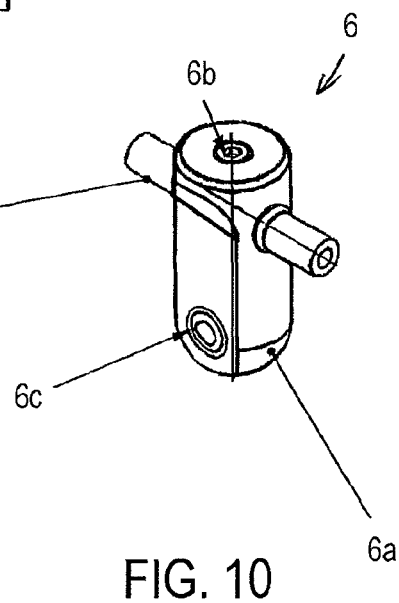
FIG. 10 is a perspective view of a second embodiment of the pressure-motion conversion element.

In contrast to the pressure-motion conversion element 3 of the first embodiment, the pressure-motion conversion element 6 according to the second embodiment comprises a membrane 6c and a lid 6d instead of the piston 3c and the plug 3d. The membrane 6c is preferably formed of a rubber material, and is fluid-tightly fitted, preferably glued in place, in the lower cross hole of the housing 6a, as is shown in FIGS. 11e and 11f. The membrane 6c has the same function as the piston 3c, i.e. it is such that it bulges outwardly upon an increase in pressure in the pressure chamber R, thus being adapted to exert force on a force measuring sensor 5b.

In contrast to the plug 3d which is provided with a seal 3f and is screwed into the housing 3a of the pressure-motion conversion element 3 of the first embodiment, the lid 6d is fluid-tightly glued in.

The pressure-motion conversion element 6 of the second embodiment cooperates with the force measuring element 5 in the same way as the pressure-motion conversion element 3 according to the first embodiment.

Although the present invention has been described with reference to a tube portion of the connecting tube 2a of the hydraulic bag, the pressure-motion conversion element may be connected or fluid-connected to another element of the lubricant supply. In this respect, the pressure-motion conversion element may also be connected or fluid-connected to a connecting tube piece that is connected to elements of the lubricant supply, such as two lubricant supply tubes.

What is claimed is:

1. A pressure gauge for one way endoscopic devices comprising:
   a pressure-motion conversion element having a movable portion for receiving a fluid pressure and effecting a movement of the movable portion in the form of a piston or a membrane in response to the change thereof; and
   a force measuring element for measuring a force exerted thereon by the movement of the movable portion;
   wherein the pressure-motion conversion element and the force measuring element are formed as preferably separate components that can be pieced together, are separated in a fluid-tight manner, and can be coupled mechanically wherein the force-measurement element comprises a housing with an orifice, within which housing a force-measuring sensor and a positioning means are arranged opposite to each other for positioning the pressure motion conversion element in a predetermined position relative to the force measuring sensor, the pressure motion conversion element being inserted with the movable portion thereof through the orifice into a fixed position between the force measuring sensor and the positioning means in the housing when the pressure gauge is in an operative state, the movable portion being in contact with the force measuring sensor.

2. The pressure gauge of claim 1, wherein:
   the pressure-motion conversion element is formed as a gas- or fluid-tight unit.

3. The pressure gauge of claim 2, wherein:
   the pressure-motion conversion element has a receiving portion for receiving a portion of a container or tube through which a pressurized gas or fluid flows, whose pressure is to be measured by the pressure gauge.

4. The pressure gauge of claim 3, further comprising:
   a disposable fluid bag storing a fluid, wherein the receiving portion receives a tube portion of a tube, which is connected to the disposable fluid bag.

5. The pressure gauge of claim 1, further comprising:
   a locking mechanism for fixing the pressure-motion conversion element in an assembled state thereof relative to the force measuring element, the locking mechanism provided on at least one of: the force measuring element and the pressure-motion conversion element.

6. The pressure gauge of claim 1, wherein: the pressure-motion conversion element has a receiving portion for receiving a portion of a container or tube through which a pressurized gas or fluid flows, whose pressure is to be measured by the pressure gauge.

7. The pressure gauge of claim 6, further comprising: a disposable fluid bag storing a fluid, wherein the receiving portion receives a tube portion of a tube, which is connected to the disposable fluid bag.

* * * * *

UNITED STATES PATENT AND TRADEMARK OFFICE
CERTIFICATE OF CORRECTION

PATENT NO.        : 7,823,457 B2                                        Page 1 of 1
APPLICATION NO.   : 12/060967
DATED             : November 2, 2010
INVENTOR(S)       : Viebach It is certified that error appears in the above-identified patent and that said Letters Patent is hereby corrected as shown below:

In column 8, line 12, delete "one way" and insert -- one-way --.

In column 8, line 15, after "portion", insert -- in the form of a piston or a membrane --.

In column 8, lines 16-17, delete "in the form of a piston or a membrane".

In column 8, line 24, after "mechanically", insert -- ; -- and start a new paragraph.

Signed and Sealed this
Eleventh Day of January, 2011

David J. Kappos
*Director of the United States Patent and Trademark Office*